United States Patent
Changoer et al.

(10) Patent No.: US 11,484,510 B2
(45) Date of Patent: Nov. 1, 2022

(54) METHOD TO TREAT VITILIGO

(71) Applicant: APIRX PHARMACEUTICAL USA, LLC, New York, NY (US)

(72) Inventors: Lekhram Changoer, Ridderkerk (NL); George Anastassov, New York, NY (US)

(73) Assignee: APIRx Pharmaceutical USA, LLC, New York, NY (US)

( * ) Notice: Subject to any disclaimer, the term of this patent is extended or adjusted under 35 U.S.C. 154(b) by 0 days.

(21) Appl. No.: 16/106,591

(22) Filed: Aug. 21, 2018

(65) Prior Publication Data

US 2019/0060252 A1 Feb. 28, 2019

Related U.S. Application Data

(60) Provisional application No. 62/550,885, filed on Aug. 28, 2017.

(51) Int. Cl.

| | |
|---|---|
| *A61K 36/00* | (2006.01) |
| *A61K 31/05* | (2006.01) |
| *A61K 31/728* | (2006.01) |
| *A61K 31/201* | (2006.01) |
| *A61K 36/24* | (2006.01) |
| *A61P 17/00* | (2006.01) |
| *A61K 36/74* | (2006.01) |
| *A61K 36/9066* | (2006.01) |
| *A61K 9/00* | (2006.01) |
| *A61K 36/58* | (2006.01) |
| *A61K 31/352* | (2006.01) |

(52) U.S. Cl.
CPC ............ *A61K 31/05* (2013.01); *A61K 9/0014* (2013.01); *A61K 31/201* (2013.01); *A61K 31/352* (2013.01); *A61K 31/728* (2013.01); *A61K 36/24* (2013.01); *A61K 36/58* (2013.01); *A61K 36/74* (2013.01); *A61K 36/9066* (2013.01); *A61P 17/00* (2018.01)

(58) Field of Classification Search
CPC .................... A61K 36/185; A61K 36/9066
USPC ................................... 424/774, 756
See application file for complete search history.

(56) References Cited

U.S. PATENT DOCUMENTS

| | | | |
|---|---|---|---|
| 2010/0298444 A1* | 11/2010 | D Az Alperi | A61K 36/9066 514/679 |
| 2013/0011484 A1* | 1/2013 | Bevier | A61K 47/10 424/491 |
| 2013/0089600 A1* | 4/2013 | Winnicki | A61K 9/127 424/450 |
| 2014/0193349 A1* | 7/2014 | Zuccolo | A61K 8/42 424/70.6 |
| 2016/0235661 A1 | 8/2016 | Changoer et al. | |
| 2019/0307719 A1* | 10/2019 | Karelis | A61K 36/899 |

FOREIGN PATENT DOCUMENTS

| | | |
|---|---|---|
| GB | 2542797 A | 4/2017 |
| WO | WO2013006729 A2 | 1/2013 |
| WO | WO2017027553 A1 | 2/2017 |

OTHER PUBLICATIONS

Huerta-Angeles et al., 26th European Conference on Biomaterials, liverpool, Aug. 31-Sep. 3, 2014.*
Kim, J.S., et al. "Cannabinoid Receptors: Their Impact in Epidermal Differentiation and Possible Role in Treatment of Psoriasis", J. Am. Acad. Derm., vol. 72, No. 5, 8, p. 1097, May 2015.
Ono, S. et al. "Coexistent Skin Lesions of Vitiligo and Psoriasis Vulgaris. Immunohistochemical Analyses for IL-17A-Producing Cells and Regulatory T Cells", Acta Derm Venerol 2014; 94:329-330.

* cited by examiner

*Primary Examiner* — Michael V Meller
(74) *Attorney, Agent, or Firm* — Swidler Law Group, LLC; Sean S. Swidler

(57) ABSTRACT

A method to treat the skin condition vitiligo is described in this invention. The method comprises topical application of a composition containing cannabinoids, in particular cannabidiol and cannabigerol, at a concentration of 3%-20% by weight of the composition onto the affected skin area of a subject in need thereof. Application may be twice (2) daily for about six (6) weeks. Cannabidiol and cannabigerol may be sourced naturally or synthetically.

13 Claims, No Drawings

METHOD TO TREAT VITILIGO

CROSS-REFERENCE TO RELATED APPLICATIONS

This application claims the benefit of U.S. Provisional Application No. 62/550,885, filed Aug. 28, 2017. Each of the above-referenced patent applications is incorporated by reference in its entirety.

BACKGROUND OF THE INVENTION

Field of the Invention

This invention concerns the field of treatment for skin conditions caused by the alterations in immune system. Various such skin conditions exist and various methods have been introduced for their treatment.

In particular, this invention concerns a method to treat vitiligo using a topical composition for application on affected skin areas.

Description of the Related Technology

The *cannabis* plant has many naturally occurring substances that are of great interest in the fields of science and medicine. Isolated compounds from the *cannabis* plant include $\Delta^9$-tetrahydrocannabinol (THC), cannabidiol (CBD), cannabichromene (CBC), cannabigerol (CBG), cannabinol (CBN), cannabidivarin (CBDV), among many other compounds. While THC has psychoactive effects, CBD, CBC, CBG, and CBDV do not. Isolated alkaloid compounds from the *cannabis* plant are called cannabinoids. There are about one hundred and forty-one (141) cannabinoids that have been isolated from the *cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

Cannabinoids can be isolated by extraction or cold pressing from *cannabis* plants. Plants in the *cannabis* genus include *Cannabis sativa, Cannabis ruderalis*, and *Cannabis indica*. These plants are natural sources of cannabinoids. Cannabinoids are also available in synthetic forms. Methods to synthesize cannabinoids in lab setting were discovered and are still currently practiced. Synthetic cannabinoids are more targeted, in that the synthetic compound usually comes isolated without other cannabinoids and/or other compounds mixed in.

Nabilone (racemic(6aR, 10aR)-1-hydroxy-6,6-dimethyl-3-(2-methyl octan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((–)-(6aR,10aR)-6,6,9-trimethyl-3-pentyl-6a, 7,8,10a-tetrahydro-6H-benzo[c]chromen-1-01)). The U.S. Food and Drug Administration approved nabilone and dronabinol for treatment of chemotherapy-induced nausea and vomiting and later for cachexia due to HIV/AIDS. In the United States, nabilone is marketed under the name Cesamet® and dronabinol under the name Marinol®. There are also generic versions of the drugs available on the market.

The IUPAC nomenclature of THC is (–)-(6aR,10aR)-6,6,9-trimethyl-3-pentyl-6a,7,8,10a-tetrahydro-6H-benzo[c]chromen-1-ol. CBD's IUPAC nomenclature is 2-((1 S,6 S)-3-methyl-6-(prop-1-en-2-yl)cyclo-hex-2-enyl)-5-pentyl-benzene-1,3-diol). CBC has the IUPAC nomenclature of 2-methyl-2-(4-methylpent-3-enyl)-7pentyl-5-chromenol. CBG has the IUPAC nomenclature of 2-[(2E)-3,7-dimethyl octa-2,6-dienyl]-5-pentyl-benzene-1,3-diol. These are among the most prominent compounds in the family of compounds extracted from the *cannabis* plant referred to as cannabinoids.

Cannabidiol (CBD) is a major phytocannabinoid, accounting for up to 40% of the plant's extract. CBD is a CB-1 receptor antagonist, while THC is a CB-1 receptor agonist. A 2010 research found that *cannabis* strains with higher concentration of CBD did not produce the short-term memory impairment normally seen in high THC *cannabis* strain, a characteristic attributed to the CB-1 receptor antagonist nature of CBD. CBD is considered to have a wider scope of medical applications than THC.

Because it is a relatively unknown cannabinoid, cannabigerol (CBG) remains understudied and its effects are only just starting to become elucidated. CBG is a non-psychoactive cannabinoid found in the *cannabis* plant. All cannabinoids in the early stage of the *cannabis* plant's life begin as CBG. CBG is found in higher concentrations in hemp plants as opposed to marijuana plants, which are grown to have higher concentrations of tetrahydrocannabinol (THC). CBG has been found to act as a high affinity $\alpha_2$-adrenergic receptor agonist, a moderate affinity to $5\text{-HT}_{1A}$ receptor antagonist, and a low affinity $CB_1$ receptor antagonist. It binds with the $CB_2$ receptor, but it is currently unknown whether it acts as an agonist or antagonist.

Vitiligo is a long term skin condition characterized by lesions of the skin losing their pigment. The lesions of skin affected become white and usually have sharp margins. The hair from the skin may also become white. Inside the mouth and nose may also be involved as well as the eyes. Typically, both sides of the body are affected. Often the lesions begin on areas of skin that are exposed to the sun. It is more noticeable in people with dark skin.

Vitiligo is believed to be due to genetic susceptibility that is triggered by an environmental factor which provokes autoimmune response. This results in the destruction of skin pigment cells (melanocytes). A defect in the TYR (tyrosinase) gene is suspected as a possible mechanism of the disease. Risk factors include a family history of the condition or other autoimmune diseases, such as hyperthyroidism, alopecia areata, and pernicious anemia. Vitiligo is classified into two main types: segmental and non-segmental. Most cases are non-segmental, meaning they affect both sides; and these cases typically get worse with time. About 10% of cases are segmental, meaning they mostly involve one side of the body; and these cases do not typically worsen with time.

Vitiligo is a common disease and affects more than 200,000 individuals per year in the United States alone. Globally about 1% of the population is affected by vitiligo. The condition is chronic and may lead to psychological trauma and social withdrawal of the affected individuals.

Among the inflammatory products of NALP1 (a member of NOD-like receptor (NLR) family of proteins) are caspase 1 and caspase 7, which activate the inflammatory cytokine interleukin-10. Interleukin-10 and interleukin-18 are expressed at high levels in patients with vitiligo. In one of the mutations, the amino acid leucine in the NALP1 protein was replaced by histidine (Leu155→His). This is strong evidence that immunomodulation may play significant role in the treatment of vitiligo.

ABBREVIATIONS

CB1: Cannabinoid receptors type 1
CB2: Cannabinoid receptors type 2

CBC: Cannabichromene
CBD: Cannabidiol
CBDV: Cannabidivarin
CBG: Cannabigerol
CBN: Cannabinol
eCB: Endocannabinoid
HA: Hyaluronic acid
THC: Tetrahydrocannabinol
THCV: Tetrahydrocannabivarin
TYR: Tyrosinase

SUMMARY

The present invention provides a method to treat vitiligo using compositions containing cannabinoids, namely cannabidiol and cannabigerol. Cannabinoids are present at 3% to 20% by weight of the total composition. The composition may be gel, liquid, spray, powder, or ointment form. Cannabinoids may be sourced naturally or synthetically and may be nano-encapsulated or micro-encapsulated. Application of the topical composition may be twice daily for about six (6) weeks.

There is provided a method to treat vitiligo, the method comprises administering a topical composition containing cannabinoids onto skin areas of a subject in need thereof.

There is provided a method to treat vitiligo as above, wherein the cannabinoids are cannabidiol and cannabigerol at a total weight percent of 3% to 20% of the composition.

There is provided a method to treat vitiligo as above, wherein the cannabigerol is present at a twice to three times the weight of cannabidiol.

There is provided a method to treat vitiligo as above, wherein cannabinoids in the composition are sourced naturally.

There is provided a method to treat vitiligo as above, wherein cannabinoids in the composition are synthetic.

There is provided a method to treat vitiligo as above, wherein cannabinoids in the composition are in powder form prior to incorporation into the composition.

There is provided a method to treat vitiligo as above, wherein cannabinoids in the composition are in crystalline form prior to incorporation into the composition.

There is provided a method to treat vitiligo as above, wherein cannabinoids in the composition are microencapsulated.

There is provided a method to treat vitiligo as above, wherein cannabinoids in the composition are nanoencapsulated with particle sizes of 20 to 40 nanometers.

There is provided a method to treat vitiligo as above, wherein the composition further comprises hyaluronic acid derivative.

There is provided a method to treat vitiligo as above, wherein the hyaluronic acid derivative is sodium oleyl hyaluronate.

There is provided a method to treat vitiligo as above, wherein the composition further comprises at least one of omega-3 or omega-6 fatty acids.

There is provided a method to treat vitiligo as above, wherein the composition further comprises plant extracts.

There is provided a method to treat vitiligo as above, wherein the plant extracts are *neem, Curcuma longa, rubia cardifolia*, or *wrightia tinctorial* extract.

There is provided a method to treat vitiligo as above, wherein the composition further comprises cacao butter.

There is provided a method to treat vitiligo as above, wherein the composition is in a hydro gel form, a liquid form, a spray form, a powder form, or an ointment form.

There is provided a method to treat vitiligo as above, wherein the topical composition is applied twice daily in six weeks onto affected skin areas on a subject having vitiligo.

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol,3-(1,1-dimethylheptyl)-6,6a7,8,10,10a-hexahydro-1-1hydroxy-6,6-dimethyl-9H-dibezo[b,d]pyran-9-ol, (−)-(3S, 4S)-7-hydroxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R, 10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendiol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a low amount of THC or from *cannabis* extract using *cannabis* cultivars bred for specific cannabinoids. Cannabidiol may also be synthetic.

The word "cannabigerol" refers to cannabigerol and cannabigerol derivatives. As used in this application, cannabigerol is derived from industrial hemp extract with a trace amount of THC or from *cannabis* extract using *cannabis* cultivars bred for specific cannabinoids. Cannabigerol may also be synthetic.

The word "vitiligo" refers to the long-term skin condition characterized by patches of the skin losing their pigment. The patches of skin affected become white and usually have sharp margins.

The table below shows the primary cannabinoids in this invention, their abbreviations, and their chemical structures.

TABLE 1

Cannabidiol (CBD)

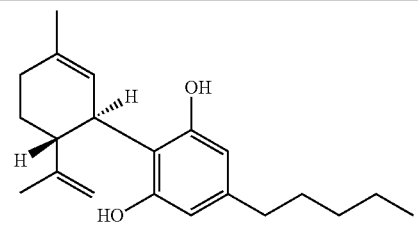 [SMILES: C=C(C)[C@@H]1CCC(C)=C[C@H]1c1c(O)cc(CCCCC)cc1O]

Cannabigerol (CBG)

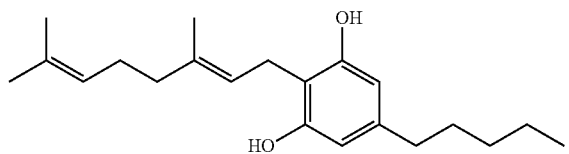 [SMILES: CCCCCc1cc(O)c(C/C=C(\C)CCC=C(C)C)c(O)c1]

Embodiments of this application relate to methods to a treat skin condition caused by altered immune system response, namely vitiligo. The methods presented concern using topical application of compositions containing cannabinoids, in particular CBD and CBG, onto affected skin areas in a subject present with or having vitiligo.

In embodiments, the medicament used in this method of treatment may be a composition such as an oil, an ointment, a cream, or a powder containing cannabinoids, namely CBD and CBG, while other cannabinoids may be present. Cannabinoid oil may be from cannabis or hemp extraction and decarboxylated to reach desired cannabinoid concentrations. CBG may be present at twice to three times the amount of CBD by weight in this composition.

In embodiments, the medicament used for this method of treatment may be a topical composition such as an oil, an ointment, a cream, or a powder containing cannabinoids, namely CBD and CBG, while other cannabinoids may be present. Cannabinoid oil may be from cannabis or hemp extraction and concentrated to reach desired cannabinoid concentrations. Cannabinoids may be decarboxylated during preparation to turn cannabinoid-acid into cannabinoids. After extraction from cannabis or hemp plant materials, cannabinoid extraction may be blended with other vegetable oils, such as hemp seed oil, sesame oil, coconut oil, among other suitable oils, to achieve desired concentration and/or viscosity. Blended vegetable oils containing cannabinoids may also be used to formulate other topical compositions.

In embodiments, cannabinoid extraction may be produced from cannabis or hemp plant with a certain ratio of cannabidiol and cannabigerol naturally occurring in such plants, then blended with vegetable oil, such as hemp seed oil, to give a cannabinoid oil with desired concentrations of cannabidiol and cannabigerol to be used in this invention.

In embodiments, cannabinoid topical compositions for use in this invention may be prepared by preparing separate cannabinoid oils or solutions with different primary cannabinoids before the various cannabinoid oils or solutions may be combined to give the final cannabinoid topical composition. For example, CBD-rich oil may be prepared at a certain concentration and CBG-rich oil may be prepared at a certain concentration separately. The oil may then be blended together to achieve desired cannabinoid concentrations and used in topical application. The oils may also be incorporated into a cannabinoid topical composition with other ingredients. The oils may also be blended together before being incorporated into a topical composition.

In embodiments, CBG may be present at about twice to three times the amount of CBD by weight in this topical composition. Other weight ratios between CBG and CBD in this cannabinoid oil are contemplated.

In embodiments, cannabinoid compositions used in this method may contain CBD/CBG oil at 3%-20% by weight. The percentages given may include both cannabinoids, for example the total weight percentage of CBD/CBG in the composition is 15%, as used in the experiment below. CBG may be present at twice to three times the amount of CBD in the same composition, even though other weight ratios between CBG and CBD are contemplated. Other cannabinoids may be present at lower concentration, such as lower than 2% or 1% by weight of the total composition. It is contemplated that CBD/CBG composition at 3%-20% by weight percent of the total composition may be used in this treatment method according to embodiments. Preferably, CBD/CBG concentration in the topical composition use comprises more than 10% by weight of the composition.

Alternatively, cannabinoids may also be incorporated into the composition from crystalline and/or powder form. Cannabinoids used in these embodiments may at be at a high purity, such as 99% purity, but could be lower or higher. Cannabinoids concentration in the composition used in this invention may be at 0.5%-20% of the total composition by weight.

Crystalline cannabinoids may be isolated from cannabis extraction. Cannabis extraction is crystallized with C5-C12 alkane, then filtrated and vacuum dried to produce cannabinoid crystal at high purity. Crystalline cannabinoids may then be combined with vegetable oil such as hemp seed oil and used as medicament for topical application.

In embodiments, the medicament may also be a composition containing cannabinoids with additional components formulated into a composition for topical application. The cannabinoids in the formulation may be in nano-encapsulated form and the size of the particles is between 20 and 40 (nanometers) nm. The cannabinoids in these compositions may also be microencapsulated. Cannabinoids may be sourced naturally or synthetically.

In embodiments, the composition used in this method may further comprised hyaluronic acid (HA) derivatives, HA derivatives may include but is not limited to sodium oleyl hyaluronate, sodium hyaluronate, or sodium azidyl hyaluronate, among other HA derivatives. Other plant extract ingredients may be present in this composition, such as neem, Curcuma longa, rubia cardifolia, wrightia tinctorial extracts, among other plant extracts. The composition may further comprise cacao butter, wherein cannabinoids are incorporated into cacao butter prior to being synthesized into the composition. Other components in this composition according to embodiments may include omega-3 and/or omega-6 fatty acids. Cannabinoids may be combined with omega-3 and/or omega-6 fatty acid.

The composition may further comprise other ingredients to effectuate the form in which the composition may be prior to usage. The composition may be prepared into a cream, an ointment, a gel, a hydro gel, a spray, a powder, or other composition form suitable for topical application. Preparation of the topical compositions containing cannabinoids according to embodiments may be by methods commonly known in the art.

Study Design

One (1) subject with present and severe vitiligo who had received no therapy for at least six (6) weeks prior to the study was selected. The subject received treatment according to embodiments of this invention. The study was conducted on lesions present on the subject's arms. Control was by means of lesions of similar size and severity on the subject's other arm.

Cannabinoid oil used in this study was CBD/CBG oil at 3% by weight (total weight percentage of CBD and CBG in the oil was 3%) and CBD/CBG oil at 15% by weight (total weight percentage of CBD and CBG in the oil was 15%). CBD/CBG oil was supplied as a hemp seed oil ointment containing CBD and CBG from Cannabis sativa L. extract. The percentages given included both cannabinoids, such that the total weight percentage of CBD/CBG in the oil was 3% in the first oil and 15% in the second. Other cannabinoids may be present at lower concentration, such as lower than 1% by weight.

The subject was evaluated for present skin depigmentation lesions due to vitiligo to choose lesions for this study. On the left arm of each subject, two skin lesions at least twenty (20) centimeters away from each other were selected for treatment. Two (2) corresponding skin lesions on the right arm were selected for control.

Each lesion was assessed with repigmentation and comparison with the previous skin color prior to treatment.

The study was conducted by topical application of CBD/CBG oil to depigmented skin lesion present on the subject's skin. CBD/CBG oil was applied as a thin layer on the subject's skin. One lesion located on the left arm received topical application of CBD/CBG oil at 15% by weight of the total composition, the other lesion of the left arm received topical application of CBD/CBG oil at 3% by weight of the total composition. In these oils, CBG were present at twice the amount of CBD by weight. Two lesions on the right arm were selected and received placebo (0% CBD/CBG oil) to serve as controls.

Preparation of CBD/CBG Oil

Cannabis sativa L. plants are grown, harvested, and processed to produce a botanical extract with naturally occurring cannabinoids. This botanical extract is analyzed for cannabinoid content to ascertain the weight percentage of major cannabinoids, namely CBD and CBG. The botanical extract is then blended with hemp seed oil to give CBD/CBG oil ointment.

Two CBD/CBG oil types with different CBD/CBG concentrations were prepared. The first CBD/CBG oil had CBD and CBG, in combination, at 3% by weight of the total composition. The second CBD/CBG oil had CBD and CBG, in combination, at 15% by weight of the total composition. The ratio of CBG:CBD is 2:1 in each of these oil preparations.

A third oil comprised only hemp seed oil and contained no CBD, CBG, or other cannabinoids. This third oil served as placebo in this experiment.

CBG/CBD oil was supplied by Axim Biotechnologies, Inc. The CBG/CBD strains were obtained from the company Ecohemp SRL.

Drug Treatment Procedure and Administration

The subject received treatment twice daily for six (6) weeks as follows:

The subject received topical application of a thin layer of 3% CBG/CBD oil on the upper lesion and 15% CBG/CBD oil on the lower lesion of the left arm and placebo (0% CBG/CBD oil) on the two lesions of the right arm.

Scoring of the lesions was by comparing the pigment of the lesions before and after treatment.

At the endpoint of the study, results were the difference as percentage of improvement between the left and right corresponding lesions. Lesions on the right arms are control samples. The following was the result of the study as described herein.

TABLE 2

| Condition | Subject | % Improvement of 3% CBD/CBG oil | % Improvement of 15% CBD/CBG oil |
|---|---|---|---|
| Vitiligo | Subject 1 | 0 | 11 |

The outcome was remarkable in the pattern of repigmentation. In other treatment methods, repigmentation starts perifollicular or from the borders of the lesion, however in this subject a very light diffuse repigmentation occurred. The effect was temporary and disappeared a few weeks after the end of the treatment. Therefore, longer treatment might have a remarkable positive effect, especially when considering that the subject has had a therapy resistant form of vitiligo for many years.

Discussion

Treatment by 3% CBG/CBD oil showed no improvement on the lesions. The 15% CBG/CBD oil treatment showed 11% improvement on the subject. The improvement was intra-specimen, where the subject's other lesions served as their own controls.

Despite the fact that only two concentrations have been used, there seems to be a clear dose-response effect, while the higher dose was effective, the lower dose did not show any effect.

Due to the systemic penetration of the active ingredients (CBG/CBD), an overall improvement may have occurred for both the studied lesions receiving CBD/CBG oil at 3% and 15% by weight of the composition. This may have negatively influenced the perceived effectiveness of the treatment, since CBD/CBG would also have systemic effect due to the transdermal penetration.

Activation of peripheral CB1 receptors contributes to hemorrhagic and endotoxin-induced hypotension. Both CBG and CBD act as CB1 antagonists, which might suggest a possible mechanism that explains a reduction in redness in skin lesions through reduction of vasodilatation. This is supported by the finding that cannabinoids can inhibit inflammatory cytokines and angiogenic growth factors such as hypoxia inducible factor-1 α (HIF-1 α), vascular endothelial growth factor (VEGF), matrix metalo-proteinases (MMPs), basic fibroblast growth factor (bFGF), Angiopoietin-2, interleukin-8 (IL-8), IL-17, and IL-2 as well as cellular adhesion molecule 1 (ICAM-1) and vascular cell adhesion molecule-1 (VCAM-1) both in vivo and in vitro.

A popular model for understanding skin inflammation is the Th1/Th2 model for helper T cells where imbalance between Th1 and Th2 (Type 1 and Type 2 helper T cells, respectively) could explain fundamental mechanisms of dermatitis, psoriasis and vitiligo. Though there are some complicating factors to the model, like the possible influence of Th9, Th17, and Th22 in the pathology of inflammatory skin diseases, the main principle of the model is appreciated in understanding of these diseases. The results from this study indicate a possible Th1/Th2 rebalancing mechanism attributed to the cannabinoids used in the composition Despite the fact that only two concentrations have been used, there seems to be a clear dose-response effect, whereby higher doses (15% CBD/CBG oil) are effective where lower doses (3% CBD/CBG oil) do not show any effect. Factors influencing the dose effect might be a limited skin penetration, since skin penetration of cannabinoids may be poor.

The results present evidence for a possible synergistic role of CBD and CBG in dermatological conditions such as vitiligo. Restoring the Th1/Th2 balance is thought to be the key mechanism of action, with a possible additional direct inhibiting effect of CBG and CBD on melanocytic apoptosis.

CONCLUSION

These data indicate that CBG/CBD oil significantly reduces the symptoms of vitiligo. The controls receiving placebo oil did not show any improvement while CBG/CBD at higher concentration showed an improvement on vitiligo, where diffuse repigmentation occurred.

REFERENCES

Ando T, Xiao W, Gao P, Namiranian S, Matsumoto K, Tomimori Y, et al. *Critical Role for Mast Cell Stat5 Activity in Skin Inflammation*. Cell Reports. 6(2):366-76.

Biedermann T, Skabytska Y, Kaesler S, Volz T. *Regulation of T Cell Immunity in Atopic Dermatitis by Microbes: The Yin and Yang of Cutaneous Inflammation*. Frontiers in Immunology. 2015; 6(353).

Biro T, Toth B I, Hasko G, Paus R, Pacher P. *The Endocannabinoid System of The Skin in Health and Disease: Novel Perspectives and Therapeutic Opportunities*. Trends in Pharmacological Sciences. 2009; 30(8):411-20.

Borrelli F, Fasolino I, Romano B, Capasso R, Maiello F, Coppola D, et al. *Beneficial Effect of the Non-Psychotropic Plant Cannabinoid Cannabigerol on Experimental Inflammatory Bowel Disease*. Biochemical Pharmacology. 2013; 85(9):1306-16.

Borrelli F, Pagano E, Romano B, Panzera S, Maiello F, Coppola D, et al. *Colon Carcinogenesis is Inhibited by The TRPM8 Antagonist Cannabigerol, a Cannabis-Derived Non-Psychotropic Cannabinoid*. Carcinogenesis. 2014; 35(12):2787-97.

Brenneisen R, Egli A, Elsohly M A, Henn V, Spiess Y. *The Effect of Orally and Rectally Administered Delta 9-Tetrahydrocannabinol on Spasticity: a Pilot Study With 2 Patients*. International Journal of Clinical Pharmacology and Therapeutics. 1996; 34(10):446-52.

Campos A C, Moreira F, Gomes F V, Del Bel E A, Guimarães F S. *Multiple Mechanisms Involved in the Large-Spectrum Therapeutic Potential of Cannabidiol in Psychiatric Disorders*. Philosophical Transactions of the Royal Society of London Series B, Biological Sciences. 2012; 367(1607):3364-78.

Cascio M, Gauson L, Stevenson L, Ross R, Pertwee R. *Evidence that the Plant Cannabinoid Cannabigerol is a Highly Potent A(2) Adrenoceptor Agonist and Moderately Potent 5HT(IA) Receptor Antagonist*. Br. J. Pharmacol. 2010; 159(1):129-41.

Cheng Y, Hitchcock S A. *Targeting Cannabinoid Agonists for Inflammatory and Neuropathic Pain*. Expert Opinion on Investigational Drugs. 2007; 16(7):951-65.

Cuba L F, Salum F G, Cherubini K, Figueiredo M A. *Cannabidiol: An Alternative Therapeutic Agent for Oral Mucositis?* Journal of Clinical Pharmacy and Therapeutics. 2017.

Ezzedine K, Eleftheriadou V, Whitton M, van Geel N. *Vitiligo*. Lancet. 2015; 386(9988): 74-84.

Iseger T A, Bossong M G. *A Systematic Review of The Antipsychotic Properties of Cannabidiol in Humans*. Schizophrenia Research. 2015; 162(1-3):153-61.

Jäger A, Dardalhon V, Sobel R A, Bettelli E, Kuchroo V K. *Th1, Th17 and Th9 Effector Cells Induce Experimental Autoimmune Encephalomyelitis with Different Pathological Phenotypes*. Journal of Immunology (Baltimore, Md.: 1950). 2009; 183(11):7169-77.

Kinghorn A D, Falk H, Gibbons S, Kobayashi J. *Phytocannabinoids: Unraveling the Complex Chemistry and Pharmacology of Cannabis sativa*: Springer International Publishing; 2017.

Lambert D M, Fowler C J. *The Endocannabinoid System: Drug Targets, Lead Compounds, and Potential Therapeutic Applications*. Journal of Medicinal Chemistry. 2005; 48(16):5059-87.

Maccarrone M, Bab I, Biro T, Cabral G A, Dey S K, Di Marzo V, et al. *Endocannabinoid Signaling at the Periphery: 50 Years After THC*. Trends in Pharmacological Sciences. 2015; 36(5):277-96.

McGilveray I J. *Pharmacokinetics of Cannabinoids*. Pain Research & Management. 2005; 10 Suppl A:15a-22a.

Mechoulam R, Peters M, Murillo-Rodriguez E, Hanuš L O. *Cannabidiol—Recent Advances*. Chemistry & Biodiversity. 2007; 4(8):1678-92.

Raphael I, Nalawade S, Eagar T N, Forsthuber T G. *T Cell Subsets and Their Signature Cytokines in Autoimmune and Inflammatory Diseases*. Cytokine. 2015; 74(1):5-17.

Russo E B, Burnett A, Hall B, Parker K K. *Agonistic Properties of Cannabidiol at 5-HT1a Receptors*. Neurochemical Research. 2005; 30(8): 1037-43.

Ryberg E, Larsson N, Sjögren S, Hjorth S, Hermansson N, Leonova J, et al. *The Orphan Receptor GPR55 is a Novel Cannabinoid Receptor*. Br. J. Pharmacol. 2007; 152(7): 1092-101.

Small-Howard A L, Shimoda L M, Adra C N, Turner H. *Anti-Inflammatory Potential of CB1-Mediated Camp Elevation in Mast Cells*. The Biochemical Journal. 2005; 388(Pt 2):465-73.

Sugawara K, Biro T, Tsuruta D, Toth B I, Oroningo A, Zakany N, et al. *Endocannabinoids Limit Excessive Mast Cell Maturation and Activation in Human Skin*. The Journal of Allergy and Clinical Immunology. 2012; 129 (3):726-38.e8.

Toh M R, Teo V, Kwan Y H, Raaj S, Tan S Y, Tan J Z. *Association Between Number of Doses Per Day, Number of Medications and Patient's Non-Compliance, and Frequency of Readmissions in a Multi-Ethnic Asian Population*. Preventive Medicine Reports. 2014; 1:43-7.

Turcotte C, Blanchet M R, Laviolette M, Flamand N. *The CB2 Receptor and Its Role as a Regulator of Inflammation*. Cellular and Molecular Life Sciences: CMLS. 2016; 73(23):4449-70.

Valdeolivas S, Navarrete C, Cantarero I, Bellido M L, Munoz E, Sagredo O. *Neuroprotective Properties of Cannabigerol In Huntington's Disease: Studies in R6/2 Mice and 3-Nitropropionate-Lesioned Mice*. Neurotherapeutics: The Journal of the American Society for Experimental NeuroTherapeutics. 2015; 12(1):185-99.

Varga K, Wagner J A, Bridgen D T, Kunos G. *Platelet-and Macrophage-Derived Endogenous Cannabinoids are Involved in Endotoxin-Induced Hypotension*. FASEB Journal: Official Publication of the Federation of American Societies for Experimental Biology. 1998; 12(11): 1035-44.

Weiss L, Zeira M, Reich S, Har-Noy M, Mechoulam R, Slavin S, et al. *Cannabidiol Lowers Incidence of Diabetes in Non-Obese Diabetic Mice*. Autoimmunity. 2006; 39(2): 143-51.

Whitton M E, Pinart M, Batchelor J, Leonardi-Bee J, Gonzalez U, Jiyad Z, et al. *Interventions for Vitiligo*. The Cochrane Database of Systematic Reviews. 2015(2): Cd003263.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein

What is claimed is:

1. A method of treating vitiligo in a human in need thereof consisting essentially of topically administering to the human in need thereof about 15 wt. % of cannabidiol and cannabigerol, wherein the human is administered low or trace amounts of $\Delta^9$ tetrahydrocannabinol and wherein the cannabigerol is present at a twice to three times the weight of the cannabidiol.

2. The method of claim 1, wherein the cannabidiol and cannabigerol are from a natural source.

3. The method of claim 1, wherein the cannabidiol and cannabigerol are synthetic.

4. The method of claim 1, wherein the cannabidiol and cannabigerol are in powder form prior to use.

5. The method of claim 1, wherein the cannabidiol and cannabigerol are in crystalline form prior to use.

6. The method of claim 1, wherein the cannabidiol and cannabigerol are microencapsulated.

7. The method of claim 1, wherein the cannabidiol and cannabigerol are nanoencapsulated with particle sizes of 20 nanometers to 40 nanometers.

8. The method of claim 1, wherein the cannabidiol and cannabigerol further consists essentially of sodium oleyl hyaluronate.

9. The method of claim 1, wherein the cannabidiol and cannabigerol further consist of at least one of omega-3 fatty acids or omega-6 fatty acids.

10. The method of claim 1, wherein the cannabidiol and cannabigerol further consist essentially of neem extract, *Curcuma longa* extract, *rubia* cardifolia extract, or *wrightia* tinctorial extract.

11. The method of claim 1, wherein the cannabidiol and cannabigerol further consist essentially of cacao butter.

12. The method of claim 1, wherein the cannabidiol and cannabigerol are in a hydro gel form, a liquid form, a spray form, a powder form, or an ointment form.

13. The method of claim 1, wherein the cannabidiol and cannabigerol are applied twice daily for six weeks onto the affected skin areas of a human suffering from vitiligo.

* * * * *